(12) United States Patent
Amagi et al.

(10) Patent No.: US 12,310,786 B2
(45) Date of Patent: May 27, 2025

(54) ULTRASONIC DIAGNOSTIC APPARATUS AND ULTRASONIC DIAGNOSTIC METHOD

(71) Applicant: Canon Medical Systems Corporation, Otawara (JP)

(72) Inventors: Seina Amagi, Nasushiobara (JP); Shingo Toyoda, Utsunomiya (JP); Minori Ohashi, Otawara (JP); Masashi Usumura, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 147 days.

(21) Appl. No.: 18/048,089

(22) Filed: Oct. 20, 2022

(65) Prior Publication Data

US 2023/0125118 A1  Apr. 27, 2023

(30) Foreign Application Priority Data

Oct. 21, 2021 (JP) .................................. 2021-172463
Sep. 30, 2022 (JP) .................................. 2022-158565

(51) Int. Cl.
*A61B 8/08* (2006.01)
*A61B 8/00* (2006.01)
(Continued)

(52) U.S. Cl.
CPC ............ *A61B 8/0866* (2013.01); *A61B 8/462* (2013.01); *A61B 8/488* (2013.01); *A61B 8/5246* (2013.01);
(Continued)

(58) Field of Classification Search
CPC ....... A61B 8/0866; A61B 8/462; A61B 8/488; A61B 8/5246; A61B 8/5261; A61B 8/54;
(Continued)

(56) References Cited

U.S. PATENT DOCUMENTS

| 5,976,088 A * | 11/1999 | Urbano ............... G01S 7/52063 600/443 |
| 2010/0324422 A1* | 12/2010 | Wanda ................. A61B 8/5238 600/443 |

(Continued)

FOREIGN PATENT DOCUMENTS

JP   2020-501679 A   1/2020

OTHER PUBLICATIONS

Zeng, W. et al., "Design and Experiment of Online Monitoring System for Long-Term Culture of Embryo", Journal of Biomedical Engineering, vol. 38, No. 6, 2021, (with English Translation), 27 pages.

*Primary Examiner* — Hien N Nguyen
(74) *Attorney, Agent, or Firm* — Oblon, McClelland, Maier & Neustadt, L.L.P.

(57) ABSTRACT

According to one embodiment, an ultrasonic diagnostic apparatus includes an ultrasonic probe and processing circuitry. The ultrasonic probe is configured to transmit and receive an ultrasonic wave. The processing circuitry is configured to acquire an optical image of a subject housed in a housing unit containing a medium. The processing circuitry is configured to estimate state information of the subject from the optical image. The processing circuitry is configured to set a scan condition of ultrasonic scanning for the subject based on the state information.

18 Claims, 8 Drawing Sheets

(51) Int. Cl.
*G01S 7/52* (2006.01)
*G01S 15/89* (2006.01)

(52) U.S. Cl.
CPC .............. *A61B 8/5261* (2013.01); *A61B 8/54* (2013.01); *G01S 7/52053* (2013.01); *G01S 15/8934* (2013.01)

(58) Field of Classification Search
CPC ........... A61B 8/42; A61B 8/085; A61B 8/543; A61B 8/5223; G01S 7/52053; G01S 15/8934; G01S 7/52079; G01S 15/8979; G01S 15/8915; G01S 15/899
See application file for complete search history.

(56) References Cited

U.S. PATENT DOCUMENTS

| | | | |
|---|---|---|---|
| 2014/0091140 A1* | 4/2014 | Hieronimi .............. | G06K 7/146 235/375 |
| 2016/0135782 A1* | 5/2016 | Chen .................... | A61B 8/0875 600/440 |
| 2017/0251954 A1* | 9/2017 | Lotan .................. | A61B 5/0002 |
| 2018/0366033 A1* | 12/2018 | Buckman ............. | G09B 23/303 |
| 2019/0380900 A1 | 12/2019 | Flake et al. | |

* cited by examiner

ULTRASONIC DIAGNOSTIC APPARATUS AND ULTRASONIC DIAGNOSTIC METHOD

CROSS-REFERENCE TO RELATED APPLICATIONS

This application is based upon and claims the benefit of priority from Japanese Patent Applications No. 2021-172463, filed Oct. 21, 2021; and No. 2022-158565, filed Sep. 30, 2022; the entire contents of all of which are incorporated herein by reference.

FIELD

Embodiments described herein relate generally to an ultrasonic diagnostic apparatus and an ultrasonic diagnostic method.

BACKGROUND

In recent years, research has been conducted in the practical application of an extrauterine environment system, which is a so-called artificial uterus. An extrauterine environment system is a system in which a mammalian fetus is contained in a container filled with artificial amniotic fluid, which is circulated to supply oxygen and nutrients and remove waste products, to grow the fetus outside a mother's body.

In such a system, there is a need to perform ultrasonic examinations using a fixed ultrasonic probe in order to monitor the health of the fetus, especially in vivo. However, in fixed-point ultrasonic examinations, scan conditions initially determined for ultrasonic scanning, such as a field of view (FOV) and a focal position, may no longer be suitable for an observation target region due to body movements and growth of the fetus within the container. Thus, in order to image with sufficient image quality and FOV for monitoring, it is necessary to change the ultrasonic scan conditions on a case-by-case basis.

DETAILED DESCRIPTION

In general, according to one embodiment, An ultrasonic diagnostic apparatus includes an ultrasonic probe and processing circuitry. The ultrasonic probe is configured to transmit and receive an ultrasonic wave. The processing circuitry is configured to acquire an optical image of a subject housed in a housing unit containing a medium. The processing circuitry is configured to estimate state information of the subject from the optical image. The processing circuitry is configured to set a scan condition of ultrasonic scanning for the subject based on the state information.

Hereinafter, the ultrasonic diagnostic apparatus, the ultrasonic diagnostic method, and the ultrasonic diagnostic program according to the present embodiment will be described with reference to the drawings. In the following embodiments, elements assigned the same reference numeral perform the same operation, and redundant descriptions will be omitted as appropriate. An embodiment will be described below with reference to the drawings.

First Embodiment

Figure 1:
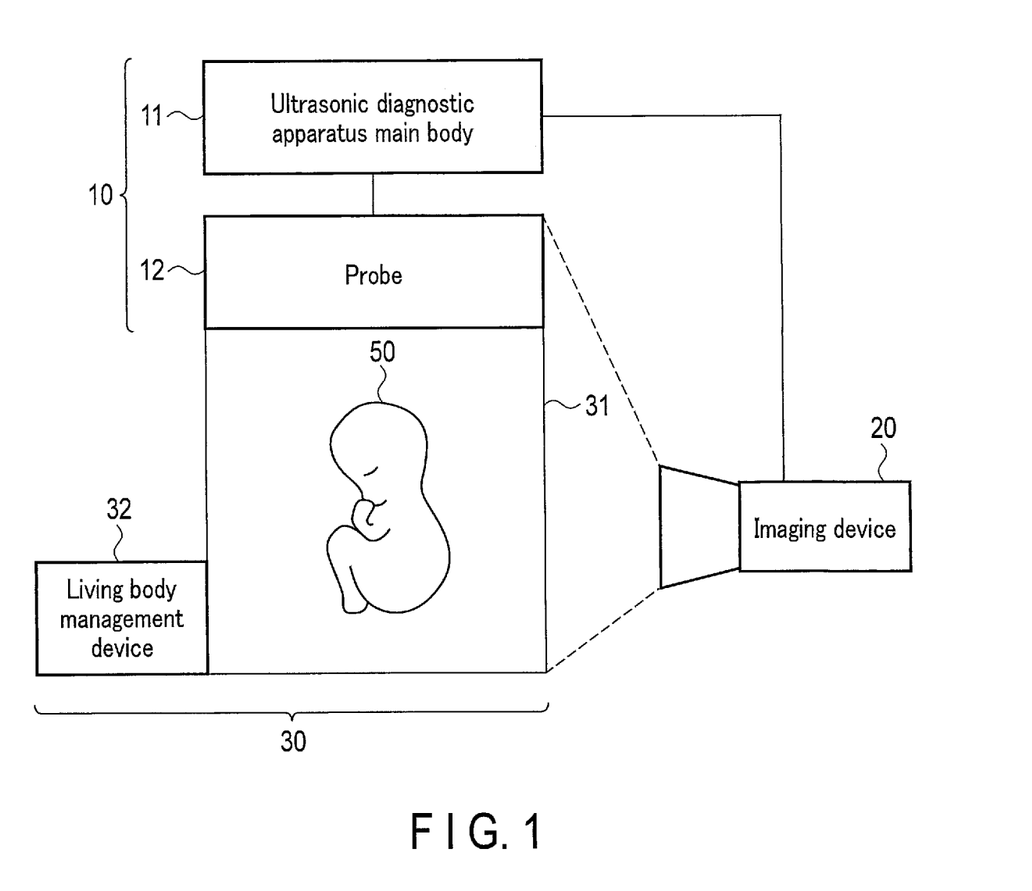
FIG. 1 is a conceptual diagram showing an example of a use of an ultrasonic diagnostic apparatus for an artificial uterus system.

FIG. 1 is a diagram showing an example of a use of an ultrasonic diagnostic apparatus according to the present embodiment. Here, it is assumed that an ultrasonic diagnostic device 10 and an imaging device 20 are used to diagnose a condition of a subject 50 housed in a so-called extrauterine environment system 30. In the present embodiment, a fetus is assumed as the subject 50, but any living organism that grows and acts in a liquid or is cultured in a liquid may be used as the subject 50.

The extrauterine environment system 30, also called an artificial uterus, includes a housing unit 31 and a living body management device 32.

The housing unit 31 is a container for housing the subject 50, and is internally filled with a liquid. In the present embodiment, the subject 50 is assumed to be a fetus, so the housing unit 31 is filled internally with artificial amniotic fluid. If the subject 50 is to be grown, the housing unit 31 should be designed to be large enough to accommodate the subject 50 after growth. The housing unit 31 is assumed to be formed of a flexible material such as polyethylene film that can be optically imaged from the outside, but it can also be formed of a material that can be optically imaged but is rigid such as glass or plastic.

The living body management device 32 is connected to the housing unit 31 and performs control to deliver nutrients and oxygen into the housing unit 31 and remove unnecessary substances. The supply of nutrients and oxygen and the removal of unnecessary substances are performed, for example, via a tube that is inserted into the housing unit 31.

The ultrasonic diagnostic apparatus 10 includes an ultrasonic diagnostic apparatus main body 11 and an ultrasonic probe 12. The ultrasonic diagnostic apparatus main body 11 transmits a control signal to the ultrasonic probe 12 according to an ultrasonic scan condition. The ultrasonic diagnostic apparatus main body 11 receives a reception signal related to a reflected wave from the ultrasonic probe 12, and generates an ultrasonic image.

Assuming that the ultrasonic probe 12 is fixed to the housing unit 31 and is installed in a stationary position, the ultrasonic probe 12 is installed so that its ultrasonic wave transmitting and receiving surface is in contact with the housing unit 31 so that the entire housing unit 31 can be imaged. For example, the ultrasonic probe 12 is a linear probe in which a plurality of vibrators are arranged along a predetermined direction. The ultrasonic probe 12 may be shaped like a flat sheet so that the interior of the housing unit 31 can be imaged over a larger range. That is, the ultrasonic probe can be of any shape, such as a convex probe, as long as it can image to cover at least a position within the housing unit 31 where the subject 50 may be located.

The ultrasonic probe 12 transmits an ultrasonic signal toward the inside of the housing unit 31, and receives a reflected wave of the transmitted ultrasonic signal. If the housing unit 31 is formed of a hard material such as glass, a surface where the ultrasonic probe 12 and the housing unit 31 come into contact should be formed of a material having less effect on the transmission and reception of ultrasonic waves, such as a flexible material.

An imaging device 20, also called an optical imaging unit, optically images the housing unit 31 and generates optical imaging data including the subject 50. Optical imaging data is, for example, an optical image (camera image) or video. The imaging device 20 may be, for example, a general camera formed of an imaging element, or may be an infrared camera capable of imaging in the dark. The imaging device 20 may be arranged outside the housing unit 31 and capable of imaging the housing unit 31 from the outside, or may be arranged inside the housing unit 31 and capable of imaging the subject 50 from the inside. However, if the imaging device 20 is arranged inside, the imaging device 20 is arranged in a position where it can image the entire housing unit 31.

Next, a configuration example of the ultrasonic diagnostic apparatus 10 will be described with reference to FIG. 2.

The ultrasonic diagnostic apparatus 10 of FIG. 1 includes the ultrasonic diagnostic apparatus main body 11 (hereinafter, simply referred to as the apparatus main body 11) and the ultrasonic probe 12. The apparatus main body 11 is connected to an input device 102 and an output device 103. The apparatus main body 11 is connected to an external device 104 via a network NW. The external device 104 is, for example, a server equipped with a picture archiving and communication systems (PACS) and a workstation capable of executing post processing.

The ultrasonic probe 12 executes, for example, ultrasonic scanning on a scan area in a living body P, which is a subject, under control of the apparatus main body 11. The ultrasonic probe 12 includes, for example, an acoustic lens, one or more matching layers, a plurality of vibrators (piezoelectric elements), a backing material, etc. The acoustic lens is formed of, for example, silicone rubber, and converges ultrasonic beams. The one or more matching layers perform impedance matching between the plurality of vibrators and the living body. The backing material prevents propagation of ultrasonic waves backward in a radial direction from the plurality of vibrators. The ultrasonic probe 12 is detachably connected to the apparatus main body 11. The ultrasonic probe 12 may be provided with a button which is to be pressed at the time of an offset process, an operation of freezing an ultrasonic image (freeze operation), etc.

The plurality of vibrators generate ultrasonic waves based on a drive signal supplied from an ultrasonic transmission circuitry 110 to be described later included in the apparatus main body 11. Thereby, the ultrasonic waves are transmitted from the ultrasonic probe 12 to the living body P. Upon the ultrasonic waves being transmitted from the ultrasonic probe 12 to the living body P, the transmitted ultrasonic waves are sequentially reflected on an acoustic impedance discontinuous surface of a body tissue of the living body P, and are received as reflected wave signals by the plurality of piezoelectric vibrators. An amplitude of the received reflected waves depends on a difference in acoustic impedance on the discontinuous surface to which the ultrasonic waves are reflected. If a transmitted ultrasonic pulse is reflected by a blood flow or a surface of the cardiac wall, etc. that is in motion, a frequency of the reflected wave signal is shifted due to the Doppler effect according to the moving object's velocity component in a direction of ultrasonic transmission. The ultrasonic probe 12 receives the reflected wave signal from the living body P, and converts the reflected wave signal into an electric signal.

FIG. 1 illustrates a connection relationship between a single ultrasonic probe 12 and the apparatus main body 11. However, a plurality of ultrasonic probes can be connected to the apparatus main body 11. Which of the connected ultrasonic probes is to be used for the ultrasonic scanning can be selected discretionarily by using, for example, a software button on a touch panel to be described later.

The apparatus main body 11 is an apparatus that generates an ultrasonic image based on a reflected wave signal received by the ultrasonic probe 12. The apparatus main body 11 includes the ultrasonic transmission circuitry 110, an ultrasonic reception circuitry 120, an internal storage circuitry 130, an image memory 140, an input interface 150, an output interface 160, a communication interface 170, and a processing circuitry 180.

The ultrasonic transmission circuitry 110 is a processor that supplies a drive signal to the ultrasonic probe 12. The ultrasonic transmission circuitry 110 is realized by, for example, a trigger generation circuit, a delay circuit, a pulsar circuit, etc. The trigger generation circuit repeatedly generates a rate pulse for forming a transmission ultrasonic wave at a predetermined rate frequency. The delay circuit gives a delay time for each of the plurality of piezoelectric vibrators to each rate pulse generated by the trigger generation circuit. This delay time is required to converge the ultrasonic waves generated from the ultrasonic probe into a beam to determine a transmission directivity. The pulsar circuit applies drive signals (drive pulses) to the plurality of ultrasonic vibrators provided in the ultrasonic probe 12 at timings based on the rate pulses. The transmission direction from the surfaces of the plurality of piezoelectric vibrators can be discretionarily adjusted by varying the delay time given to each rate pulse by the delay circuit.

The ultrasonic transmission circuitry 110 can discretionarily change an output intensity of the ultrasonic wave by the drive signal. In the ultrasonic diagnostic apparatus, an influence of attenuation of ultrasonic waves in the living body P can be reduced by increasing the output intensity. The ultrasonic diagnostic apparatus can acquire a reflected wave signal having a large S/N ratio at the time of reception by reducing the influence of ultrasonic wave attenuation.

In general, when an ultrasonic wave is propagated inside the living body P, a strength (also referred to as an "acoustic power") of vibration of the ultrasonic wave corresponding to the output intensity is attenuated. The attenuation of the acoustic power is caused by absorption, scattering, reflection, etc. Also, a degree of reduction of the acoustic power depends on a frequency of the ultrasonic wave and a distance of the ultrasonic wave in a radiation direction. For example, the degree of attenuation is increased by increasing the frequency of the ultrasonic wave. Further, the longer the distance of the ultrasonic wave in the radiation direction, the greater the degree of attenuation.

The ultrasonic reception circuitry 120 is a processor that performs various processing on a reflected wave signal received by the ultrasonic probe 12 to generate a reception signal. The ultrasonic reception circuitry 120 generates a reception signal corresponding to a reflected wave signal of an ultrasonic wave acquired by the ultrasonic probe 12. Specifically, the ultrasonic reception circuitry 120 is realized by, for example, a preamplifier, an A/D converter, a demodulator, a beamformer (adder), etc. The preamplifier performs gain correction by amplifying, for each channel, the reflected wave signals received by the ultrasonic probe 12. The A/D converter converts the gain-corrected reflected wave signal into a digital signal. The demodulator demodulates the digital signal. The beam former gives, to the demodulated digital signal, a delay time required to determine a reception directivity, and adds a plurality of digital signals with delay times given. Through the addition process of the beam former, a reception signal with an enhanced reflected component in a direction corresponding to the reception directivity is generated. The reception signal may also be referred to as an IQ signal. Further, the ultrasonic reception circuitry 120 may store the reception signal (IQ signal) in the internal storage circuitry 130 to be described later, or may output the reception signal to the external device 104 via the communication interface 170.

The internal storage circuitry 130 includes, for example, a storage medium which is readable by a processor, such as a magnetic or optical storage medium or a semiconductor memory. The internal storage circuitry 130 stores therein a program for realizing ultrasonic transmission/reception, a program and various data related to transmit aperture synthesis control processing to be described later, etc. The programs and various data may be, for example, pre-stored in the internal storage circuitry 130. Alternatively, the programs and various data may be, for example, stored and distributed in a non-volatile storage medium, and may be read from the non-volatile storage medium and installed into the internal storage circuitry 130. In addition, the internal storage circuitry 130 stores B-mode image data, contrast image data, image data related to blood flow images, etc. generated by the processing circuitry 180 according to an operation input from the input device 102 via the input interface 150. The internal storage circuitry 130 can transfer the stored image data to the external device 104, etc. via the communication interface 170. The internal storage circuitry 130 may store the reception signal (IQ signal) generated by the ultrasonic reception circuitry 120, or may transfer the reception signal to the external device 104, etc. via the communication interface 170.

The internal storage circuitry 130 may be a drive device, etc. which reads and writes various information to and from a portable storage medium such as a CD drive, a DVD drive, and a flash memory. The internal storage circuitry 130 can write the stored data into the portable storage medium, and store the data in the external device 104 via the portable storage medium.

The image memory 140 includes, for example, a storage medium which is readable by a processor, such as a magnetic or optical storage medium, or a semiconductor memory. The image memory 140 stores image data corresponding to a plurality of frames immediately before a freeze operation input via the input interface 150. The image data stored in the image memory 140 is successively displayed (cine-displayed), for example.

The above-described internal storage circuitry 130 and image memory 140 may not necessarily be realized by independent storage devices. The internal storage circuitry 130 and the image memory 140 may be realized by a single storage device. The internal storage circuitry 130 and the image memory 140 may each be realized by a plurality of storage devices.

The input interface 150 receives various instructions from an operator via the input device 102. The input device 102 is, for example, a mouse, a keyboard, a panel switch, a slider switch, a trackball, a rotary encoder, an operation panel, or a touch command screen (TCS). The input interface 150 is connected to the processing circuitry 180 via a bus, for example, so that it can convert an operation instruction that is input by the operator, into an electric signal, and output the electric signal to the processing circuitry 180. The input interface 150 is not limited to the one connected to the physical operation components such as a mouse and a keyboard. Examples of the input interface include a circuit that receives an electric signal corresponding to an operation instruction that is input from an external input device provided separately from the ultrasonic diagnostic apparatus 10 and outputs this electric signal to the processing circuitry 180.

The output interface 160 is, for example, an interface for outputting an electric signal from the processing circuitry 180 to the output device 103. The output device 103 is a discretionary display such as a liquid crystal display, an organic EL display, an LED display, a plasma display, or a CRT display. The output device 103 may be a touch-panel display that can also serve as the input device 102. In addition to the display, the output device 103 may further include a speaker that outputs audio. The output interface 160 is connected to the processing circuitry 180 via a bus, for example, and outputs an electric signal from the processing circuitry 180 to the output device 103.

The communication interface 170 is, for example, connected to the external device 104 via the network NW, and performs data communications with the external device 104.

The processing circuitry 180 is, for example, a processor that functions as the core of the ultrasonic diagnostic apparatus 10. The processing circuitry 180 executes a program stored in the internal storage circuitry 130, thereby realizing a function corresponding to that program. The processing circuitry 180 includes, for example, a B-mode processing function 181, a Doppler processing function 182, an image generation function 183, an acquisition function 184, an estimation function 185, a setting function 186, a determination function 187, a display control function 188, and a system control function 189.

The B-mode processing function 181 is a function to generate B-mode data based on a reception signal received from the ultrasonic reception circuitry 120. With the B-mode processing function 181, the processing circuitry 180 performs, for example, an envelope wave detecting process, a logarithmic compressing process, etc. on a reception signal received from the ultrasonic reception circuitry 120 to generate data (B-mode data) that expresses a signal intensity with luminance. The generated B-mode data is stored in a RAW data memory (not shown) as B-mode RAW data on a two-dimensional ultrasonic scanning line (raster).

The Doppler processing function 182 is a function to generate data (Doppler information) as an extraction of Doppler effect-based motion information of a moving object that is present within a region of interest (ROI) set in a scan region, and this data is generated through a frequency analysis of the reception signal received from the ultrasonic reception circuitry 120. The generated Doppler information is stored in the RAW data memory (not shown) as Doppler RAW data (also referred to as Doppler data) on a two-dimensional ultrasonic scanning line.

Specifically, with the Doppler processing function 182, the processing circuitry 180 estimates an average velocity, an average dispersion value, an average power value, etc., for example, as motion information of a moving object at each of a plurality of sample points to generate Doppler data showing the estimated motion information. The moving object is, for example, a blood flow, a tissue of a cardiac wall, etc., and a contrast agent. The processing circuitry 180 according to the first embodiment, with the Doppler processing function 182, estimates an average blood flow velocity, a blood flow velocity dispersion value, a power value of a blood flow signal, etc. as blood flow motion information (blood flow information) at each of the sample points to generate Doppler data showing the estimated blood flow information.

The image generation function 183 is a function to generate B-mode image data based on the data generated with the B-mode processing function 181. For example, the processing circuitry 180, with the image generation function 183, converts (scan-converts) a scanning line signal sequence of ultrasonic scanning into a scanning line signal sequence of a video format representatively used by television, etc. to generate image data for display (display image data). Specifically, the processing circuitry 180 executes RAW-pixel conversion, e.g., coordinate conversion according to a scanning form of ultrasonic waves by the ultrasonic probe 12, for B-mode RAW data stored in the RAW data memory, thereby generating two-dimensional B-mode image data (also referred to as ultrasonic image data) composed of pixels. In other words, the processing circuitry 180, with the image generation function 183, generates a plurality of ultrasonic images (medical images) respectively corresponding to a plurality of consecutive frames from ultrasonic image data acquired through execution of ultrasonic scanning based on a scan condition set by the setting function 186 to be described later. The image generation function 183 may also generate an optical image based on optical imaging data.

The processing circuitry 180, for example, generates Doppler image data in which blood flow information is visualized by performing a RAW-pixel conversion on the Doppler RAW data stored in the RAW data memory. The Doppler image data is average velocity image data, dispersion image data, power image data, or image data obtained by a combination thereof. As the Doppler image data, the processing circuitry 180 generates color Doppler image data in which blood flow information is displayed in color and Doppler image data in which one piece of blood flow information is displayed in a wavy shape on a gray scale. The color Doppler image data is generated when a blood flow image mode described above is executed.

The acquisition function 184 acquires an optical image of the subject from the imaging device 20.

The estimation function 185 estimates state information of the subject from the optical image. The state information is information related to the state of the subject in the housing unit 31, and includes, for example, at least one of a size, a position, or a posture of the subject.

The setting function 186 sets a scan condition of ultrasonic scanning for the subject based on the state information.

The determination function 187 performs various determination processing, e.g., determines whether or not the state information of the subject satisfies a predetermined condition.

The display control function 188 is a function to display an image based on various pieces of ultrasonic image data generated with the image generation function 183 on a display, which is the output device 103. Specifically, for example, the processing circuitry 180 controls, with the display control function 188, display on a display of an image based on B-mode image data, contrast image data, or image data including both of them, generated with the image generation function 183. Display of an optical image is also controlled with the display control function 188.

More specifically, the processing circuitry 180, with the display control function 188, for example, converts (scan-converts) a scanning line signal sequence of ultrasonic scanning into a scanning line signal sequence in a video format representatively used by television, etc. to generate display image data. In addition, the processing circuitry 180 may perform various processing, such as dynamic range, brightness, contrast, y curve correction, and RGB conversion, on the display image data. The processing circuitry 180 may also add supplementary information, such as textual information of various parameters, a scale, or a body mark, to the display image data. The processing circuitry 180 may also generate a user interface (GUI: Graphical User Interface) for an operator to input various instructions through the input device, and display the GUI on a display.

The system control function 189 is a function to control operations of the entire ultrasonic diagnostic apparatus 10 in an integrated manner. For example, the ultrasonic transmission circuitry 110 and the ultrasonic reception circuitry 120 are controlled so as to perform ultrasonic scanning based on transmission and reception conditions set with the setting function.

Figure 2:
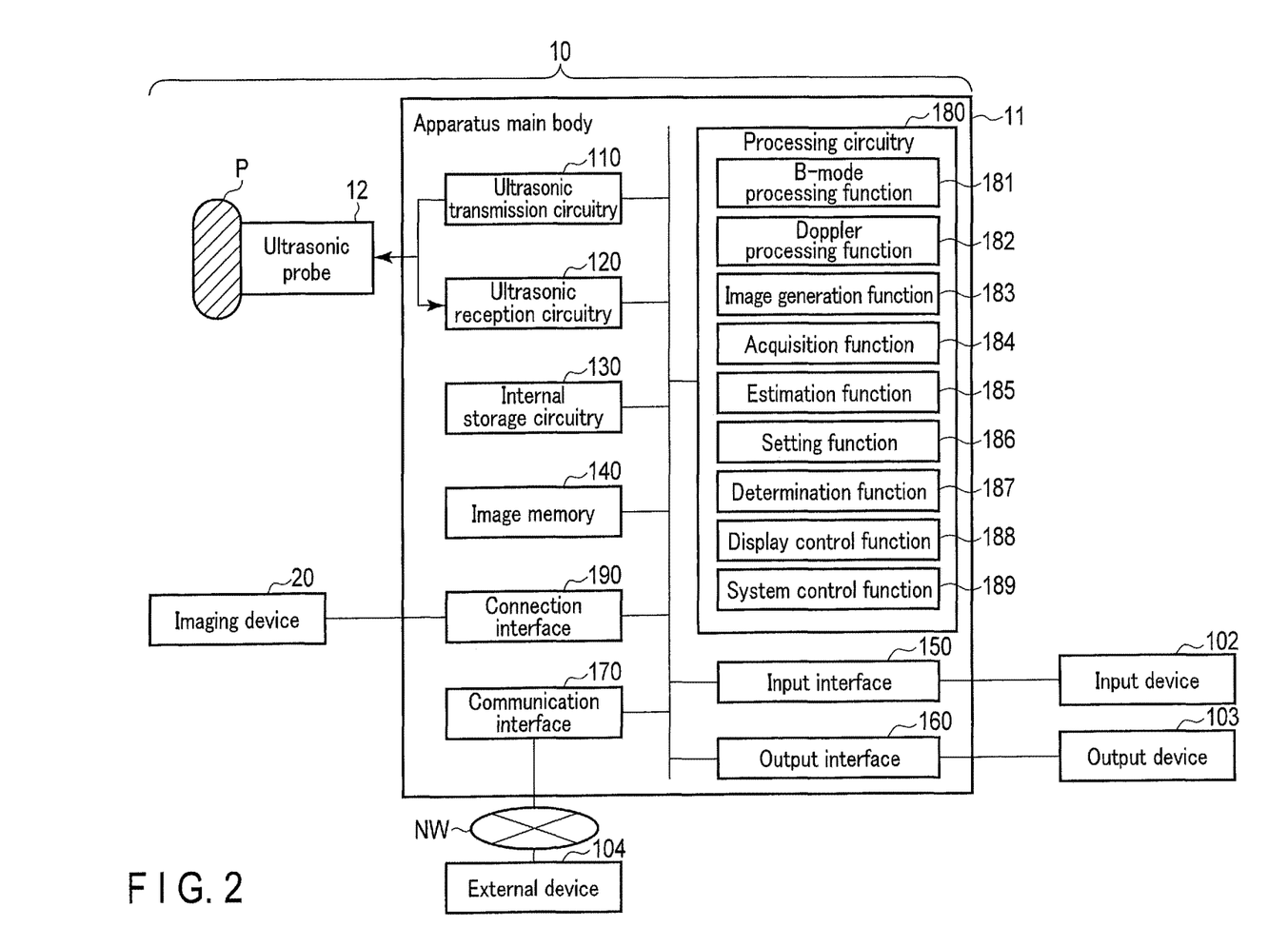
FIG. 2 is a diagram showing a configuration example of the ultrasonic diagnostic apparatus.

In the example shown in FIG. 2, the processing circuitry 180 includes the estimation function 185 and the determination function 187, but the configuration is not limited thereto. The estimation function 185 and the determination function 187 may be included in a separate image processing circuitry (not shown) within or connected to the imaging device 20 and the processing according to the present embodiment may be performed.

The connection interface 190 is connected to the imaging device 20, and performs data communications of optical imaging data, etc. between the imaging device 20 and the apparatus main body 11.

Figure 3:
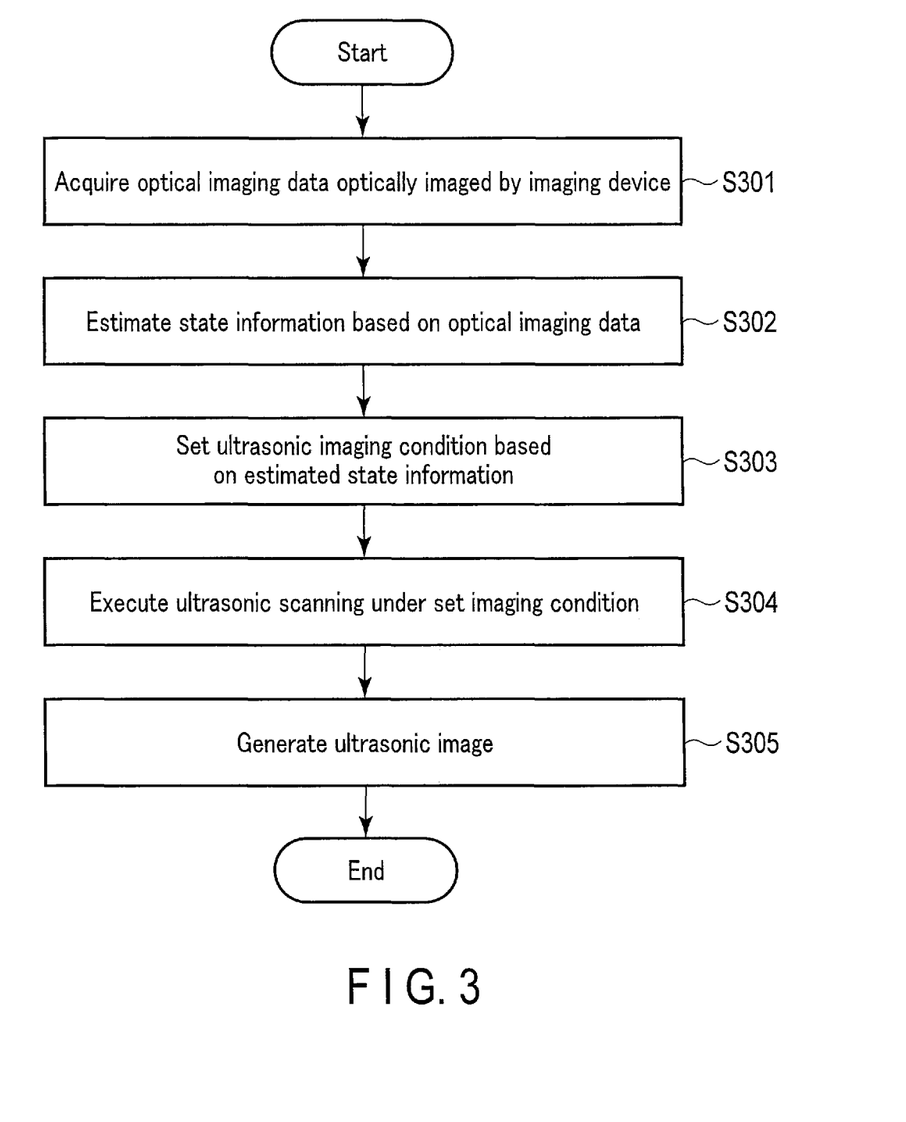
FIG. 3 is a flowchart showing an operation example of an ultrasonic diagnostic apparatus according to a first embodiment.

Next, an operation example of the ultrasonic diagnostic apparatus 10 according to the first embodiment will be described with reference to the flowchart of FIG. 3.

In step S301, the processing circuitry 180, with the acquisition function 184, acquires optical imaging data such as an optical image or an infrared image from the imaging device 20. The optical imaging data may be data captured by the imaging device 20 at a timing indicated by the user, or may be data captured at a predetermined interval such as once an hour or once a day. The imaging device 20 may also be set to perform so-called automatic monitoring and perform imaging if the subject is in a predetermined body position or present in a predetermined position. Optical imaging data captured if the subject is in a predetermined body position or present in a predetermined position may be used.

In step S302, the processing circuitry 180, with the estimation function 185, estimates state information of the subject based on the optical imaging data. The state information includes, for example, at least one of a size of the subject, a posture of the subject, or a position indicating where the subject is present in the housing unit 31. With the estimation function 185, the processing circuitry 180 may, for example, pre-calculate a distance per pixel size of an optical image and estimate the size of the subject from the number of vertical and horizontal pixels of the subject depicted in the optical image.

The posture of the subject can be determined by, for example, preparing multiple outline templates associated with possible postures of the subject and performing a pattern matching process to detect whether or not a subject image matching those outline templates exists on the optical image. A subject image detected by the pattern matching process as having a similarity to an outline template that is equal to or greater than a threshold value can be estimated to have a posture of the similar outline template.

Since the entire housing unit 31 is captured in the optical image, the position of the subject in the housing unit can be estimated, for example, by detecting the position of the subject on the optical image.

A timing for estimating state information can be, for example, when optical imaging data is acquired or if a user instruction for an optical image is received from the user. The user instruction is, for example, an instruction to set an ROI for the subject depicted in the optical image.

In step S303, the processing circuitry 180, with the setting function 186, sets scan conditions of ultrasonic scanning based on the estimated state information. The scan conditions include, for example, ultrasonic transmission and reception conditions such as an angle of view, a depth, a region of interest (ROI), a focal position, and a frame rate, and imaging modes such as a B mode and a Doppler mode. A specific example of scan condition setting will be described later with reference to FIG. 4.

In step S304, the processing circuitry 180, with the system control function 189, acquires ultrasonic data by executing ultrasonic scanning under the conditions set in step S303.

In step S305, the processing circuitry 180, with the image generation function 183, generates an ultrasonic image based on the ultrasonic data acquired through the ultrasonic scanning.

Next, an example of setting a scan condition will be described with reference to FIG. 4.

Figure 4:
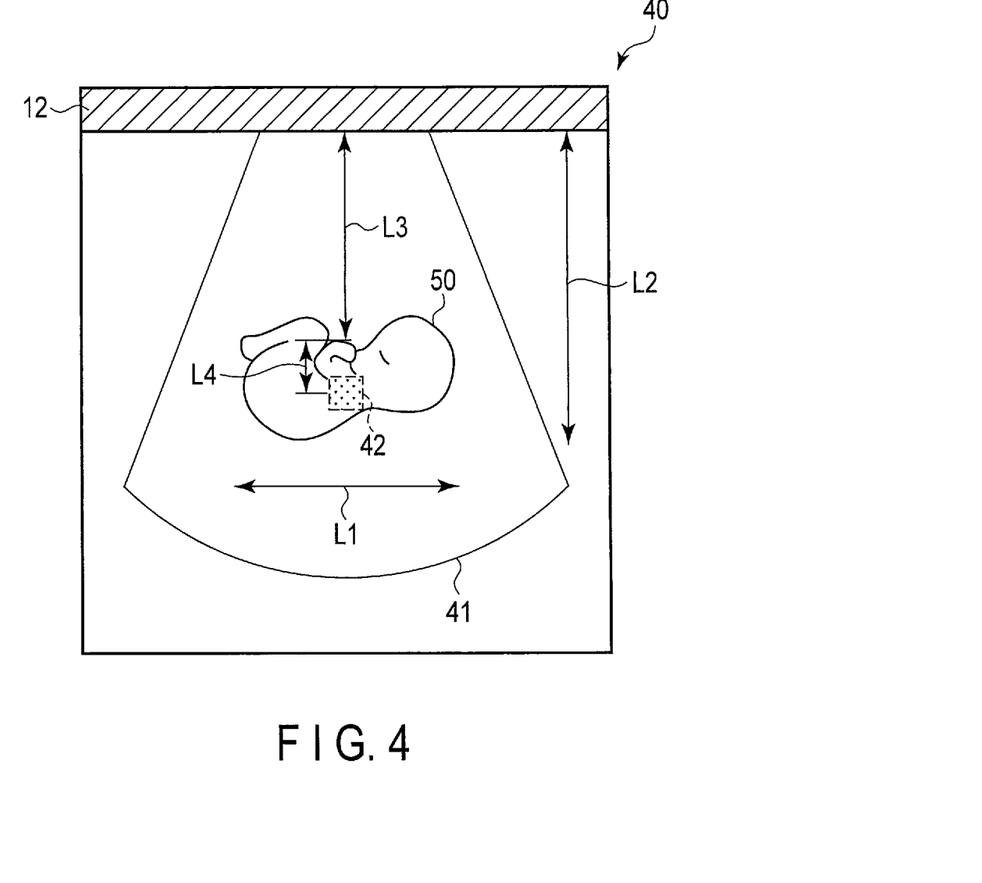
FIG. 4 is a diagram showing a setting example of a scan condition.

FIG. 4 is an example of an optical image 40 of the housing unit 31 captured by the imaging device 20.

If an angle of view is set as a scan condition, a size L1 and a position of a subject included in state information and the optical image 40 are used to estimate a distance L2 from the ultrasonic probe 12 to the farthest part of the subject 50, for example, from a distance per pixel. With the setting function 186, the processing circuitry 180 calculates an angle of view 41 required for ultrasonic scanning of the subject 50 based on the size L1 of the subject 50 and that distance L2. The angle of view 41 may be set so that the entire subject 50 is contained, or if an ROI related to the subject 50 is specified by a user, a distance to the ROI, which will be described later, may be calculated and set to include at least the ROI.

If a focal position is set as a scan condition, the processing circuitry 180, with the setting function 186, may calculate an imaging depth and/or a focal position required for ultrasonic scanning of an imaging target region from a distance L3 from the ultrasonic probe 12 to the subject 50 and a distance L4 from a body surface of the subject 50, which is a reference for defining that distance L3, to the imaging target region within the subject 50. If a depth is set, a value that is at least the distance L2 or more may be set while also considering a frame rate related to the ultrasonic scanning.

For internal structures in the living body, such as the heart and stomach, which may be set as ROIs, the distance L4 will change in depth from the body surface according to the growth over the weeks of gestation. Thus, for example, a table of a correspondence between the distance from the body surface to that internal structure and the number of weeks of pregnancy is generated in advance and if the number of weeks of the fetus can be determined, the distance L4 corresponding to that number of weeks can be obtained.

Specifically, in the example of FIG. 4, if the heart is set as ROI 42 as the internal structure of the subject 50 based on the optical image 40, a distance of ROI 42 of the subject 50 from the ultrasonic probe 12 can be calculated by calculating a sum of the distance L3 from the ultrasonic probe 12 to the subject 50 and the distance L4 determined from the number of weeks of the subject 50 with reference to the table. If the region is visible from the outside in the optical image, such as the head, arms, legs, or groin, the focal position can be determined from the optical image. If such an externally visible region is set as ROI 42, the value of distance L3 should be used as the focal position.

If a frame rate is set as a scan condition, a movement amount can be obtained by calculating, from multiple optical images of the subject 50 captured in real time, a movement amount of an imaging target region of the subject 50, for example, calculating a motion vector between the optical images. The processing circuitry, with the setting function, calculates a frame rate required to image the imaging target region of the subject (or the ROI set on the subject) based on the movement amount. For example, if the subject is awake, it is assumed that he/she moves his/her arms and legs more often than when sleeping. Therefore, by setting the frame rate according to the movement amount, an ultrasonic image with reduced blurring and improved image quality can be generated.

Alternatively, the frame rate may be determined according to the region where the ROI is set. For example, if the heart of the subject is imaged, a higher frame rate is required than in a case of imaging the face. Thus, a table that sets a correspondence between the target region of the ROI and the required frame rate may be prepared, and a frame rate for a region where an ROI is set may be set by referring to the table. The frame rates stored in the table may be values based on past setting vales or may be adjusted by the user.

The above example shows an example in which the scan conditions are set based on the state information of the subject and the ROI related to the subject, but the configuration is not limited thereto. The scan conditions may be set based on, for example, a form of the housing unit 31, etc. For example, if there is a situation that can be ascertained from an optical image, such as that the housing unit 31 is deformed and has a shape that could generate artifacts such as multiple reflections and sidelobes, the processing circuitry 180, with the setting function, may set an imaging method that reduces artifacts; for example, if it is a sidelobe artifact, an imaging mode to image using a tissue harmonic imaging (THI) method should be set as a scan condition.

As the state information, a change in facial expression of the fetus such as yawning and blinking and a frequency thereof may be included. The change in fetal facial expression and the frequency thereof may be estimated from an optical image or estimated by a trained model that has been trained through a pattern matching or a deep learning. Based on the state information on the estimated change in fetal facial expression and frequency thereof, the processing circuitry 180, with the setting function 186, may set a specific position (e.g., the brain) as an FOV of a B mode or an ROI of a color Doppler mode as a scan condition for ultrasonic scanning.

According to the first embodiment described above, an optical image is acquired by optical imaging of a subject housed in a housing unit in an extrauterine environment system using an imaging device, and state information about the subject is estimated based on the optical image. Scan conditions for ultrasonic scanning with an ultrasonic diagnostic apparatus are set based on the estimated optical information. Thereby, for a subject such as a fetus, an internal health of the living body which cannot be seen with an optical camera, such as an apical transmission image and a four-lumen cross-sectional image, can be monitored. Furthermore, although the scan conditions for ultrasonic scanning vary depending on the growth and action of the subject, appropriate scan conditions can be set without having to manually set scan conditions related to an FOV, an image quality, etc., thus generating convenient ultrasonic scanning. That is, the scan conditions can be set automatically.

Second Embodiment

A second embodiment differs in that an imaging device is activated based on ultrasonic imaging data, and optical imaging data is acquired. For example, if an anomaly occurs in a subject in a housing unit, such as arrhythmia, it cannot be recognized in an optical image, and thus the anomaly in the subject can be found by detecting the anomaly based on the ultrasonic scanning data. Arrhythmia can also be recognized by attaching an electrode of an electrocardiogram examination apparatus to the subject and acquiring an electrocardiogram (ECG) waveform, but the electrode needs to be brought into contact with the subject and hygiene risks exist in the extrauterine environment system. Ultrasonic scanning has an advantage of being able to detect an anomaly in the subject, such as arrhythmia, without contact.

Since the configuration of the ultrasonic diagnostic apparatus 10 according to the second embodiment is the same as that in the first embodiment, except for the operation of the processing circuitry 180, descriptions of the configuration will be omitted.

Figure 5:
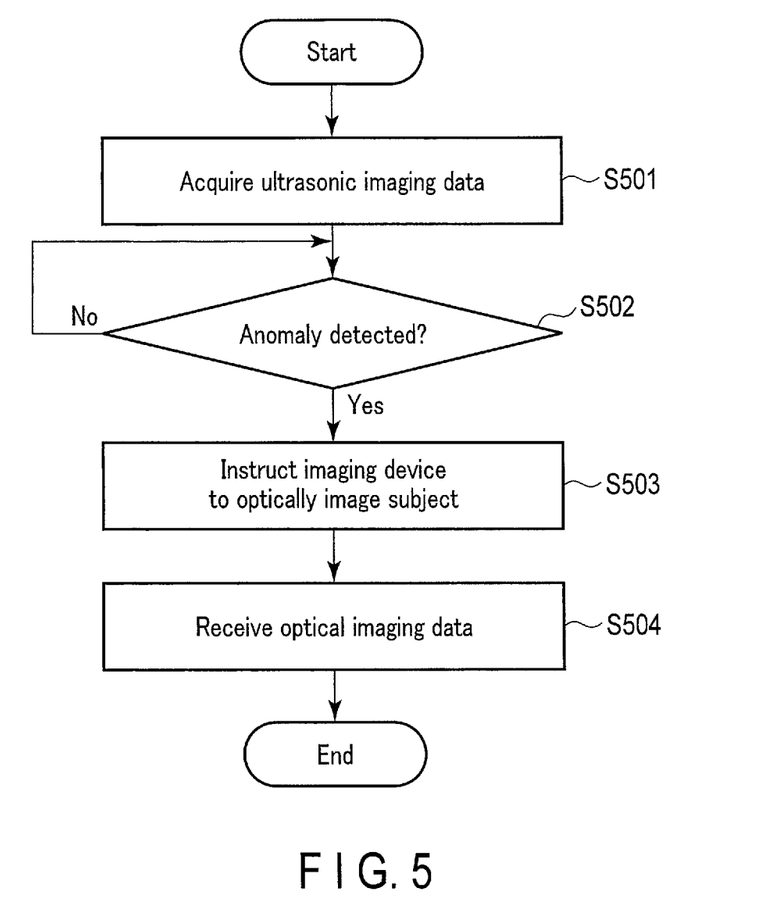
FIG. 5 is a flowchart showing an operation example of an ultrasonic diagnostic apparatus according to a second embodiment.

An operation example of the ultrasonic diagnostic apparatus 10 according to the second embodiment will be described with reference to the flowchart of FIG. 5.

In step S501, for example, the B-mode processing function 181 and the image generation function 183 of the ultrasonic diagnostic apparatus 10 ultrasonically scan the subject 50 present in the housing unit 31 and acquire ultrasonic scanning data. Here, it is assumed that ultrasonic scanning data is acquired at a predetermined sampling interval. The ultrasonic scanning data may be acquired in so-called real-time imaging, or every minute or every hour.

In step S502, the processing circuitry 180, with the determination function 187, determines whether or not an anomaly exists in the subject based on the ultrasonic scanning data. For example, a real-time ultrasonic image based on ultrasonic scanning data imaged in real time is analyzed, and if the heartbeat of the subject 50 is irregular rather than at a regular interval, it can be determined that there is an arrhythmia anomaly. If it is determined that there is an anomaly in the subject, the process proceeds to step S503; if there is no anomaly, the process of step S502 is repeated.

In step S503, the processing circuitry 180, with the system control function 189, transmits an imaging instruction to the imaging device 20 to execute optical imaging via the connection interface 190. The imaging device 20 executes optical imaging in response to that imaging instruction and acquires optical imaging data.

In step S504, the processing circuitry 180, with the acquisition function 184, receives the optical imaging data from the imaging device 20. The optical imaging data may be output directly from the imaging device 20 to an external monitor or the like.

The ultrasonic scan conditions according to the first embodiment may be set in the ultrasonic diagnostic apparatus 10 that acquired the optical imaging data in step S504. That is, if an anomaly is detected from the ultrasonic scanning data, scan conditions based on the optical imaging data can be set automatically by executing the processing in the flowchart of FIG. 3 on the optical imaging data in order to acquire a higher-quality ultrasonic image.

According to the second embodiment described above, for example, an anomaly of a subject is detected from a real-time ultrasonic image, and optical imaging of the subject by an imaging device is executed if an anomaly is detected. This allows a user to easily and quickly grasp the status of the subject because anomalies in the subject that cannot be discerned from an optical image can be detected and an optical image can be acquired by the imaging device.

By setting the scan conditions for ultrasonic scanning based on the optical image so as to feed back a result of the optical image, high-quality ultrasonic scanning data can be acquired with an appropriate angle of view, focal position, etc. set for the subject in which the anomaly occurred.

Third Embodiment

In the above-described embodiments, the state in which the ultrasonic probe 12 is fixed to the housing unit 31 is assumed, but the user may manipulate the ultrasonic probe to examine the subject 50. In this case, the ultrasonic diagnostic apparatus 10 may present to the user scan guide information, which is a guide for supporting ultrasonic imaging of the subject 50 based on the position and the posture information of the subject 50 obtained from the optical image imaged by the imaging device 20 and a current probe.

A first presentation example of the scan guide information according to the third embodiment will be described with reference to FIG. 6.

Figure 6:
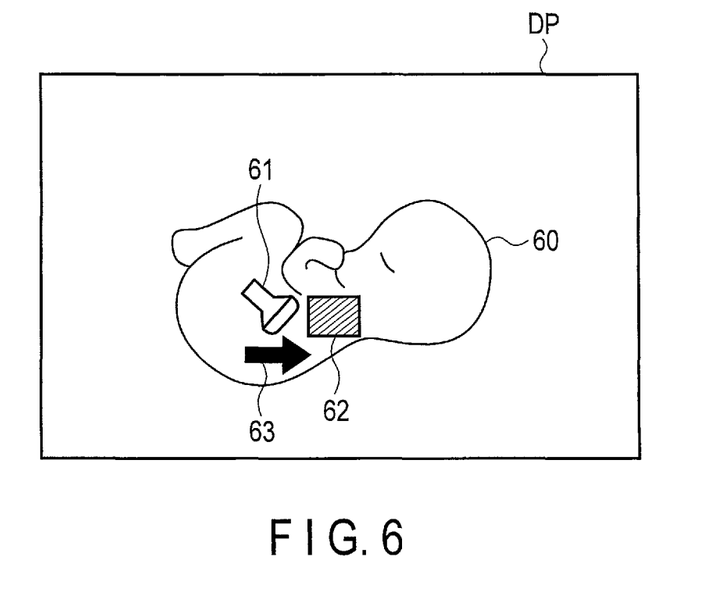
FIG. 6 is a diagram showing a first presentation example of scan guide information according to a third embodiment.

In FIG. 6, the processing circuitry 180, with the system control function 189, displays a body mark 60 indicating the subject 50 on a screen of a display, which is an example of the output device 103, as the scan guide information. Further, a probe position 61 and an examination target region 62 are displayed on the body mark 60. An annotation 63 such as an arrow indicating a scan direction of the ultrasonic probe 12 from the probe position 61 may further be displayed as the scan guide information.

In this way, by displaying the body mark 60, the probe position 61, the examination target region 62, and the annotation 63 on the screen as the scan guide information, an operator (user) can perform an intended examination while viewing the screen.

Next, a second presentation example of the scan guide information according to the third embodiment will be described with reference to FIG. 7.

Figure 7:
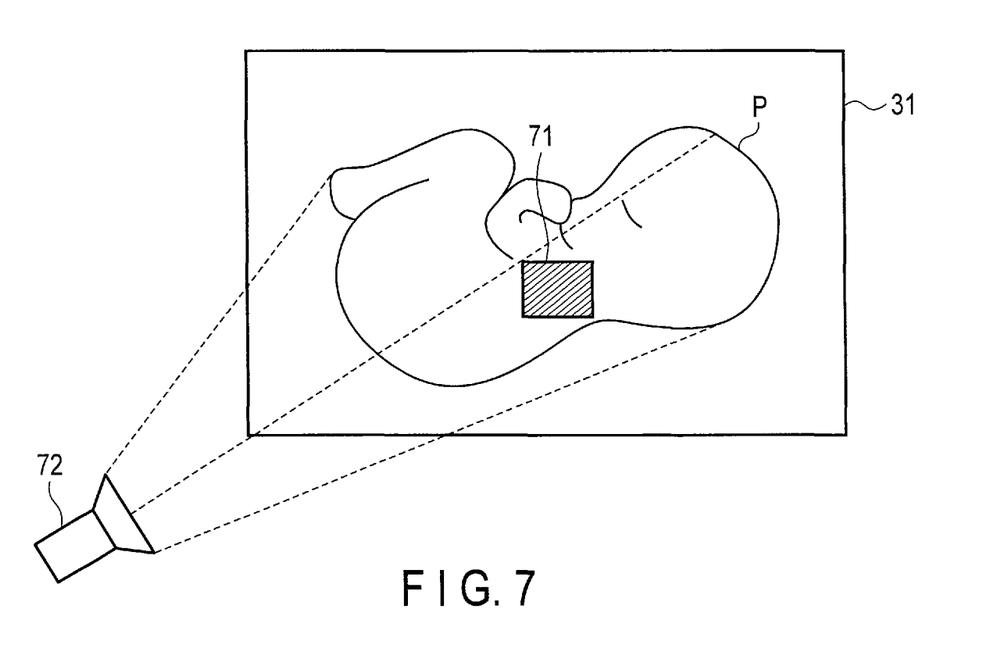
FIG. 7 is a diagram showing a second presentation example of the scan guide information according to the third embodiment.

In FIG. 7, the processing circuitry 180, with the system control function 189, superimposes an examination target region on the subject 50 by performing projection mapping on the subject 50 within the housing unit as the scan guide information. Specifically, for example, the processing circuitry 180, with the system control function 189, acquires an outline of the subject 50 to be a target for the projection mapping and a position of an imaging target region. After that, the processing circuitry 180, with the display control function 188, projects the outline of the subject 50 and an examination target region mark 71 toward the subject 50, which is housed in the housing unit 31, by projection mapping using a projector 72 capable of projecting the examination target region to superimpose them on the subject 50.

For the image on which projection mapping is performed as scan guide information, the configuration is not limited to performing projection mapping for both the outline of the subject 50 and the examination target region mark 71, as described above, but either one of the outline of the subject 50 and the examination target region mark 71 may be projected.

If the housing unit 31 is transparent, projection mapping may be performed only on, for example, the examination target region mark 71, because the state of the subject 50 inside the housing unit 31 can be seen. However, if the housing unit 31 is formed of a material with light-shielding capability, or if the housing unit 31 is covered with a material with light-shielding capability, the subject 50 may not be seen from only the examination target region mark 71, and it may be difficult to examine the subject 50. In such a case, the imaging device 20 (infrared camera) is installed inside the housing unit 31, and the position and outline information of the subject 50 are acquired with that imaging device 20 from inside the housing unit 31. The outline information here is coordinate information obtained by projecting the outline of the subject 50 onto a plane outside the housing unit 31 that serves as a projection plane. The processing circuitry 180, with the display control function 188, may perform projection mapping on the projection surface outside the housing unit 31 that is subject to projection mapping at a position corresponding to the position and outline information of the subject 50 acquired by the imaging device 20 from inside the housing unit 31.

The scan guide information may be displayed by the housing unit 31 itself emitting light. Specifically, a plurality of light-emitting elements may be arranged on the surface of the housing unit 31, and based on information from the system control function 189, the processing circuitry 180, with the display control function 188, for example, may display the information to indicate annotations such as the examination target region, the outline of the subject 50, and the scanning direction. The surface of the housing unit 31 may be formed with a transmissive display to show similar scan guide information.

Next, a third presentation example of the scan guide information according to the third embodiment will be described with reference to FIG. 8.

Figure 8:
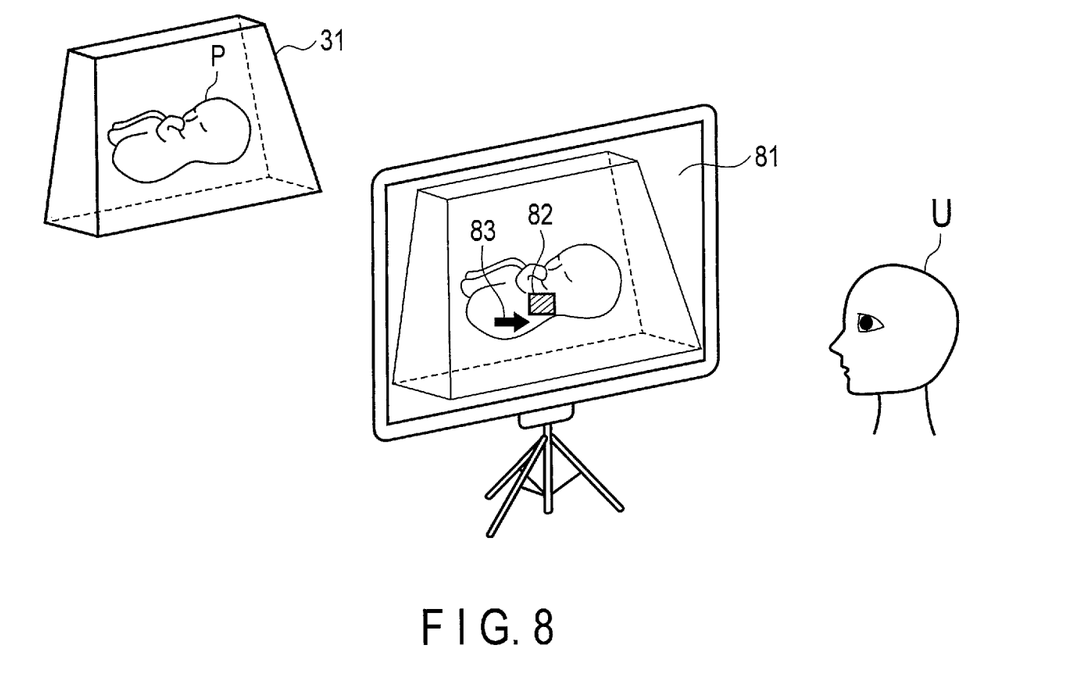
FIG. 8 is a diagram showing a third presentation example of the scan guide information according to the third embodiment.

FIG. 8 shows an example of using an augmented reality (AR) device 81 (hereinafter referred to as "AR device 81") to superimpose an annotation 83 indicating an examination target region 82 and a scanning direction, as scan guide information, on the body surface of the subject 50 in the field of view of a user U via that AR device 81. The AR device 81 is a device with a camera, such as a tablet terminal or smartphone, for example, and should be placed in a position where the user U can see and operate the ultrasonic probe 12 while viewing a screen of that AR device 81. Alternatively, if the AR device 81 is a small device such as a smartphone, it can be held in the hand. The user may operate the ultrasonic probe 12 while viewing the screen of that AR device 81.

As a method of AR display, the processing circuitry 180, with the display control function 188, transmits information on the examination target region 82 and the annotation 83 to the AR device 81, and the AR device 81 can superimpose the examination target region 82 and the annotation 83 on an image of the subject 50 housed in the housing unit 31, which is viewed by the user U through the AR device 81. Communications between the AR device 81 and the ultrasonic diagnostic apparatus 10 may be wireless or wired.

The AR device 81 may be worn by the user. An example of mounting the AR device is shown in FIG. 9.

Figure 9:
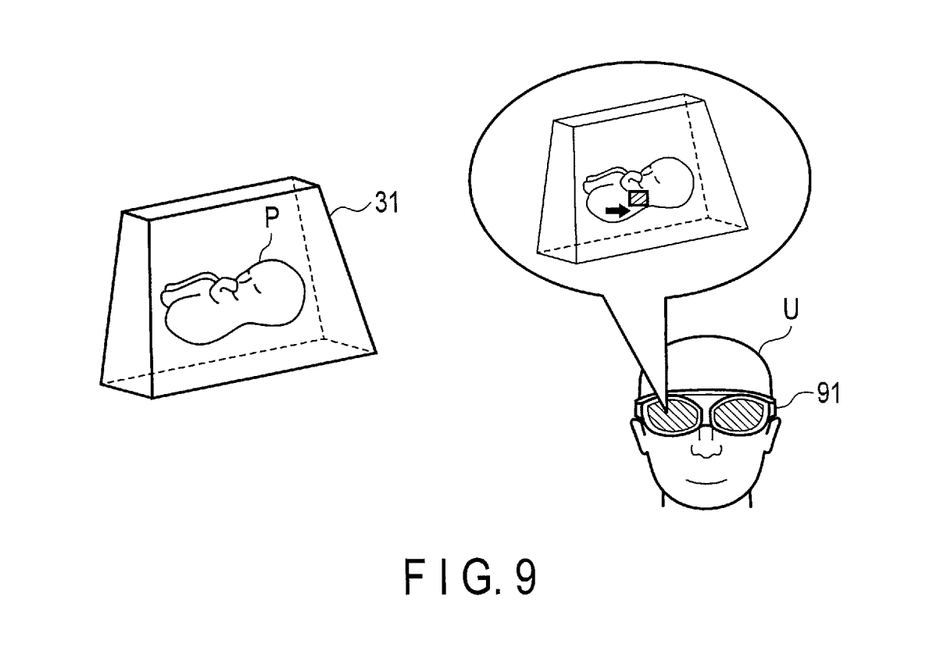
FIG. 9 is a diagram showing an example of mounting an augmented reality (AR) device.

In FIG. 9, an AR device 91 is a pair of goggles, and the user U wearing the AR device 91 can view the scan guide information displayed as in FIG. 8 through the AR device 91, the goggles.

Next, a fourth presentation example of the scan guide information according to the third embodiment will be described with reference to FIG. 10.

Figure 10:
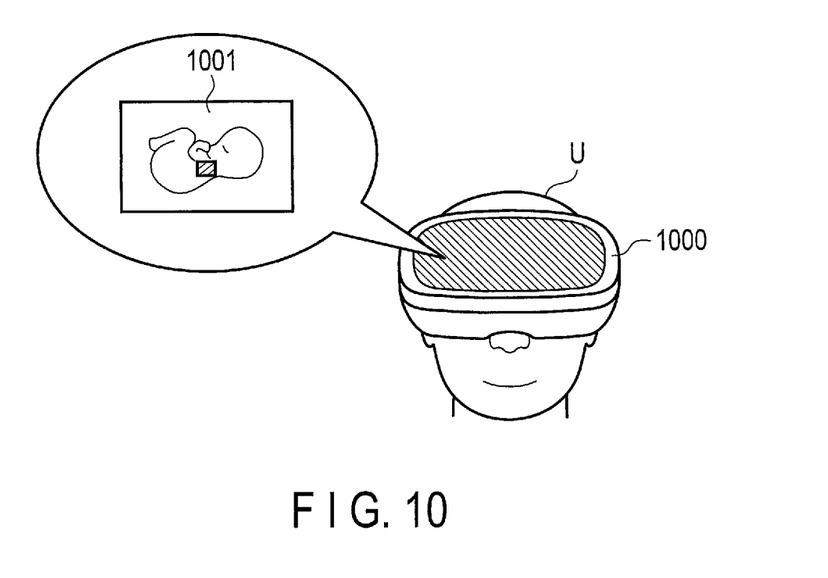
FIG. 10 is a diagram showing a fourth presentation example of the scan guide information according to the third embodiment.

In FIG. 10, scan guide information is displayed by a virtual reality (VR) generating device 1000. The VR generating device 1000 is, for example, VR goggles. The processing circuitry 180, with the system control function 189, displays, via the VR goggles worn by a user, information 1001 indicating a position of an examination target region on the body surface of the subject 50 included in that user's field of view so as to be visible to the user with the VR goggles. Communication with the ultrasonic diagnostic apparatus 10, including the system control function 189, may be wired or wireless.

According to the third embodiment described above, the user (operator) can be accurately informed of information that supports the examination of the subject 50 by displaying the scan guide information such as the annotations indicating the examination target region and the scanning direction regarding the subject 50 using the monitor, projection mapping, AR, VR, etc. Thus, the user can perform appropriate examinations while viewing the screen. That is, efficient and accurate examinations can be supported.

According to at least one embodiment described above, scan conditions can be set automatically.

In addition, the functions according to the embodiments can be implemented by installing programs for executing the above-described processing in a computer, such as a workstation, and expanding these programs in a memory. At this time, the programs that cause the computer to execute the above-described technique can be stored and distributed by means of a storage medium, such as a magnetic disk (a hard disk, etc.), an optical disk (CD-ROM, DVD, etc.), and a semiconductor memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
an ultrasonic probe configured to transmit and receive an ultrasonic wave; and
processing circuitry configured to:
acquire an optical image of a subject housed in a housing containing a medium;
estimate state information of the subject from the optical image; and set a scan condition of ultrasonic scanning for the subject based on the state information, wherein the processing circuitry is configured to calculate, as the scan condition, an angle of view required for the ultrasonic scanning of the subject based on a size of the subject and a distance from the ultrasonic probe to the subject, the distance being estimated by the size of the subject included in the state information and the optical image.

2. The ultrasonic diagnostic apparatus according to claim 1, wherein the processing circuitry is further configured to acquire scan data by executing the ultrasonic scanning using the ultrasonic probe based on the set scan condition.

3. The ultrasonic diagnostic apparatus according to claim 1, wherein the processing circuitry is further configured to report scan guide information to an operator of the ultrasonic probe based on the set scan condition set by the setting unit.

4. The ultrasonic diagnostic apparatus according to claim 3, wherein the processing circuitry is configured to perform control to display, as the scan guide information, a body mark indicating the subject on a display and information indicating a position of an examination target region on the body mark.

5. The ultrasonic diagnostic apparatus according to claim 3, wherein the processing circuitry is configured to perform control to display, as the scan guide information, an optical image of the subject on a display and information indicating a position of an examination target region on the optical image.

6. The ultrasonic diagnostic apparatus according to claim 3, wherein the processing circuitry is configured to project, as the scan guide information, information indicating a position of an examination target region on a body surface of the subject.

7. The ultrasonic diagnostic apparatus according to claim 3, wherein the processing circuitry is configured to superimpose, as the scan guide information, information indicating a position of an examination target region on a body surface of the subject using an augmented reality generating device, the body surface being included in a field of view of the augmented reality generating device.

8. The ultrasonic diagnostic apparatus according to claim 3, wherein the processing circuitry is configured to display, as the scan guide information, information indicating a position of an examination target region on a body surface of the subject displayed on virtual reality (VR) goggles worn by the operator in a manner visible by the operator with the VR goggles.

9. The ultrasonic diagnostic apparatus according to claim 1, wherein the state information includes at least one of a size, a position, a posture, a change in facial expression or a frequency of the change of the subject.

10. The ultrasonic diagnostic apparatus according to claim 1, wherein the processing circuitry is configured to set at least one of a field of view of B mode and a region of interest of a color Doppler mode based on the state information including a change of facial expression and a frequency of the change of the subject.

11. The ultrasonic diagnostic apparatus according to claim 1, wherein the processing circuitry is configured to calculate, as the scan condition, at least one of an imaging depth and a focal position required for the ultrasonic scanning of an imaging target region from a first distance and a second distance, the first distance being from the probe to the subject, and the second distance being from a body surface of the subject, which is a reference for defining the first distance, to the imaging target region inside the subject.

12. The ultrasonic diagnostic apparatus according to claim 1, wherein the processing circuitry is configured to calculate, as the scan condition, a frame rate required to scan an imaging target region based on a movement amount of the imaging target region of the subject, the movement amount being calculated from a plurality of optical images of the subject that are captured in real time.

13. The ultrasonic diagnostic apparatus according to claim 1, wherein the housing is formed of a material allowing optical imaging of the subject from outside.

14. The ultrasonic diagnostic apparatus according to claim 7, wherein the housing is formed of a flexible material and internally filled with a liquid.

15. The ultrasonic diagnostic apparatus according to claim 1, wherein the subject is a fetus.

16. The ultrasonic diagnostic apparatus according to claim 1, further comprising an optical imaging unit configured to capture the optical image.

17. An ultrasonic diagnostic method comprising:
acquiring an optical image of a subject housed in a housing containing a medium;
estimating state information of the subject from the optical image; and
setting a scan condition of ultrasonic scanning using an ultrasonic probe for the subject based on the state information;
calculating, as the scan condition, an angle of view required for the ultrasonic scanning of the subject based on a size of the subject and a distance from the ultrasonic probe to the subject, the distance being estimated by the size of the subject included in the state information and the optical image.

18. An ultrasonic diagnostic apparatus comprising:
an ultrasonic probe configured to transmit and receive an ultrasonic wave; and
processing circuitry configured to:
acquire an optical image of a subject housed in a housing containing a medium;
estimate state information of the subject from the optical image; and
set a scan condition of ultrasonic scanning for the subject based on the state information,
wherein the processing circuitry is configured to set at least one of a field of view of B mode and a region of interest of a color Doppler mode based on the state information including a change of facial expression and a frequency of the change of the subject.

* * * * *